(12) United States Patent
Hauger et al.

(10) Patent No.: US 8,049,873 B2
(45) Date of Patent: Nov. 1, 2011

(54) SURGICAL MICROSCOPY SYSTEM HAVING AN OPTICAL COHERENCE TOMOGRAPHY FACILITY

(75) Inventors: Christoph Hauger, Aalen (DE); Markus Seesselberg, Aalen (DE); Keith O'Hara, Livermore, CA (US); Yue Qiu, Pleasanton, CA (US); Xing Wei, Dublin, CA (US); Jochen M. Horn, San Francisco, CA (US); Peter Reimer, Ellwangen (DE)

(73) Assignee: Carl Zeiss Meditec AG, Jena (DE)

( * ) Notice: Subject to any disclaimer, the term of this patent is extended or adjusted under 35 U.S.C. 154(b) by 88 days.

(21) Appl. No.: 12/406,671

(22) Filed: Mar. 18, 2009

(65) Prior Publication Data
US 2009/0257065 A1    Oct. 15, 2009

Related U.S. Application Data

(60) Provisional application No. 61/070,197, filed on Mar. 19, 2008.

(51) Int. Cl.
*G01B 11/02* (2006.01)
*G01N 21/00* (2006.01)

(52) U.S. Cl. .......................... 356/73; 356/497
(58) Field of Classification Search .................. 356/456, 356/477, 479, 497, 73; 250/227.19, 227.27
See application file for complete search history.

(56) References Cited

U.S. PATENT DOCUMENTS

| | | | | |
|---|---|---|---|---|
| 5,321,501 A | * | 6/1994 | Swanson et al. | 356/479 |
| 5,359,417 A | * | 10/1994 | Muller et al. | 356/623 |
| 5,493,109 A | * | 2/1996 | Wei et al. | 250/201.3 |
| 5,657,128 A | * | 8/1997 | Muller et al. | 356/612 |
| 5,795,295 A | * | 8/1998 | Hellmuth et al. | 600/407 |
| 5,975,699 A | * | 11/1999 | Hellmuth | 351/211 |

(Continued)

FOREIGN PATENT DOCUMENTS

DE    198 37 135 A1    4/1999
(Continued)

OTHER PUBLICATIONS

Definition: zoom lens, http://web.archive.org/web/20041212042342/http://www.wordiq.com/definition/Zoom_lens, published Dec. 2004, accessed on Nov. 5, 2010, currently available at http://www.wordiq.com/definition/Zoom_lens.*

(Continued)

*Primary Examiner* — Gregory J Toatley
*Assistant Examiner* — Scott Richey
(74) *Attorney, Agent, or Firm* — Kilpatrick Townsend & Stockton LLP

(57) ABSTRACT

A surgical microscopy system is provided wherein an optical coherence tomography facility is integrated into a microscopy system. A beam of measuring light formed by collimating optics of an OCT system is deflected by a beam scanner, traverses imaging optics, and is reflected by a reflector such that the beam of measuring light traverses an objective lens of microscopy optics and is directed to an object region of the microscopy optics. A position of the beam of measuring light being incident on the reflector is substantially independent on a direction into which the beam of measuring light is deflected by the beam scanner. When traveling through the beam scanner, the beam of measuring light is comprised of a bundle of substantially parallel light rays.

17 Claims, 4 Drawing Sheets

U.S. PATENT DOCUMENTS

| | | | |
|---|---|---|---|
| 5,991,090 A | | 11/1999 | Strahle |
| 6,004,314 A * | | 12/1999 | Wei et al. ............... 606/12 |
| 6,095,648 A | | 8/2000 | Birngruber et al. |
| 6,212,006 B1 | | 4/2001 | Reiner |
| 6,377,349 B1 * | | 4/2002 | Fercher ............... 356/497 |
| 6,409,345 B1 | | 6/2002 | Molebny et al. |
| 6,550,917 B1 | | 4/2003 | Neal et al. |
| 6,736,510 B1 | | 5/2004 | Van Heugten |
| 7,022,117 B1 | | 4/2006 | Hohla et al. |
| 7,036,934 B1 | | 5/2006 | Youssefi et al. |
| 7,488,070 B2 | | 2/2009 | Hauger et al. |
| 7,692,797 B2 * | | 4/2010 | Kawahara ............... 356/497 |
| 7,699,468 B2 * | | 4/2010 | Gaida ............... 351/205 |
| 7,761,139 B2 * | | 7/2010 | Tearney et al. ............... 600/473 |
| 7,823,782 B2 * | | 11/2010 | Yatagai et al. ............... 235/454 |
| 7,839,494 B2 * | | 11/2010 | Reimer et al. ............... 356/73 |
| 7,889,423 B2 * | | 2/2011 | Reimer et al. ............... 359/368 |
| 2001/0036002 A1 | | 11/2001 | Tearney et al. |
| 2005/0241653 A1 | | 11/2005 | Van Heugten et al. |
| 2005/0243276 A1 | | 11/2005 | Van Heugten et al. |
| 2006/0066869 A1 | | 3/2006 | Ueno et al. |
| 2006/0152677 A1 | | 7/2006 | Youssefi et al. |
| 2007/0013918 A1 | | 1/2007 | Hauger et al. |
| 2007/0229760 A1 | | 10/2007 | Hirohara et al. |
| 2008/0117432 A1 | | 5/2008 | Reimer et al. |
| 2008/0117503 A1 | | 5/2008 | Reimer et al. |
| 2008/0117504 A1 | | 5/2008 | Reimer et al. |
| 2008/0186551 A1 | | 8/2008 | Hanft et al. |
| 2008/0304144 A1 | | 12/2008 | Reimer et al. |

FOREIGN PATENT DOCUMENTS

| | | | |
|---|---|---|---|
| DE | 299 05 969 U1 | | 7/1999 |
| DE | 199 50 792 A1 | | 4/2001 |
| DE | 103 60 570 A1 | | 7/2005 |
| DE | 10 2005 013 949 A1 | | 9/2006 |
| DE | 10 2005 031 496 B4 | | 1/2007 |
| DE | 10 2007 019 677 A1 | | 5/2008 |
| DE | 10 2007 019 678 A1 | | 5/2008 |
| DE | 10 2007 019 679 A1 | | 5/2008 |
| DE | 10 2007 019 680 A1 | | 5/2008 |
| EP | 0 697 611 A2 | | 2/1996 |
| EP | 0 815 801 B1 | | 1/1998 |
| EP | 0 941 692 | | 9/1999 |
| EP | 1 332 712 A1 | | 8/2003 |
| GB | 2 399 627 | | 9/2004 |
| WO | WO 01/58339 A2 | | 8/2001 |
| WO | WO 03/070090 | | 8/2003 |
| WO | WO 2005/102200 A2 | | 11/2005 |
| WO | WO 2006/052479 | | 5/2006 |
| WO | WO 2008/115060 A1 | | 9/2008 |

OTHER PUBLICATIONS

Cornejo-Rodriguez, "Chapter 9: Ronchi Test," *Optical Shop Testing*, D. Malacara, ed., Wiley, New York, 1978, pp. 283-321.

Ghozeil, "Chapter 10: Hartmann and Other Screen Tests," *Optical Shop Testing*, D. Malacara, ed., Wiley, New York, 1978, pp. 323-349.

Lankenau et al. "Combining Optical Coherence Tomography (OCT) with an Operating Microscope," *Advances in Medical Engineering* (Springer Proceedings in Physics 114), Buzug et al. eds.., Springer, Berlin, 2007, pp. 343-348.

Liang et al., "Objective Measurement of Wave Aberrations of the Human Eye," *JOSA A*, 1994; 11(7):1949-1957.

Malacara, "Chapter 11: Basic Interferometers," *Handbook of Optical Engineering*, D. Malacara et al., eds., M. Dekker, New York, 2001, pp. 339-371.

Pang et al., "Set of Two Orthogonal Adaptive Cylindrical Lenses in a Monolith Elastomer Device," *Optics Express*, 2005; 13(22):9003-9013.

Xu et al., MEMS based non-rotatory circumferential scanning optical probe for endoscopic optical coherence tomography, Proc. SPIE, 2007, vol. 6627: 662715-1-662715-11.

Search Opinion of European Patent Application No. 09003905.8, mailed Oct. 1, 2010, 6 pages total.

\* cited by examiner

10mm

SURGICAL MICROSCOPY SYSTEM HAVING AN OPTICAL COHERENCE TOMOGRAPHY FACILITY

CROSS-REFERENCES TO RELATED APPLICATIONS

This present application claims priority to U.S. Provisional Patent Application No. 61/070,197, filed on Mar. 19, 2008, the disclosure of which is hereby incorporated by reference in its entirety for all purposes.

BACKGROUND OF THE INVENTION

The present invention relates to a surgical microscopy system having an optical coherence tomography (OCT) facility. In particular, the present invention relates to a surgical microscopy system having an OCT facility, wherein a beam of measuring light is scanned across an object to be analyzed by the OCT facility.

An OCT system is for example known from EP 0 697 611 A2. A broad-band OCT-light source generates OCT-measuring light comprising different wavelengths within a certain bandwidth. A principal wavelength generated by the OCT-light source and the bandwidth of the OCT-light source determine the coherence length of the OCT-measuring light. There is a reciprocal relationship between the bandwidth of the OCT-light source and the coherence length of the OCT-measuring light generated by the OCT-light source. Two different parts of the OCT-measuring light can interferometrically only be superimposed, if a difference of optical path lengths traversed by the two different parts of OCT-measuring light is smaller than the coherence length of the OCT-light source.

Typically, a first part of the OCT-measuring light is reflected by a reference surface, such as a plane mirror, to traverse a controllable optical path length. The second part of the OCT-measuring light is directed to an object to be investigated and is reflected at regions in different depths of the object. Thus, this second part of the OCT-measuring light reflected at the object is comprised of a number of OCT-measuring light portions that have traversed different optical path lengths depending on the depth of the region of the object at which they were reflected.

In time domain OCT the reference surface is displaced, for example using a continuous movement or in a stepwise manner, such that the different OCT-measuring light portions reflected from the object interferometrically superimpose with the first part of the OCT-measuring light reflected by the reference surface at positions of the reference surface, where the OCT-measuring light portions reflected from the object have traversed an optical path length substantially equal to the optical path length traversed by the reflected first part of the OCT-measuring light. This allows to gain structural information of the object in an axial (i.e. depth) direction defined by the direction of incidence of the OCT-measuring light at the object.

To obtain structural information along an axial direction not only at a single point of the object, the second part of the OCT-measuring light needs to be scanned across a laterally extended region at the object. To achieve this, typically a scanning system is utilized including for example two mirrors spaced apart that are rotatable about axes perpendicular to each other. Thereby it is possible, to obtain a three-dimensional representation of a volume portion of the object below the surface of the object. This three-dimensional representation is in particular valuable for a surgeon to locate structure portions within the volume of the object to be manipulated, in particular useful during opthalmologic surgeries. These surgeries may be directed to regions of an anterior portion of the eye or may be directed to regions of a posterior portion of the eye. In particular, imaging the cornea by OCT and adjacent regions or imaging the retina by OCT have found widespread demand during opthalmologic surgeries.

An optical microscopy system includes an objective lens and an ocular system to image an illuminated region of an object. For this, a user may look through the ocular system to directly image the object region to his or her retina, or may look at an image acquired by a CCD camera. A CCD acquired image may be displayed to a desk monitor or may be displayed for example to a head-mounted display. In a number of known optical microscopy systems the beam path of the system is parallel downstream of the objective lens. This allows in a simple way to provide a stereoscopic optical microscopy system, wherein light emanated from the object under slightly different angles is guided downstream the objective lens to two tubular bodies harboring two oculars for the left and the right eye of the observer. Thereby, an enlarged stereoscopic imaging of the object is possible. A stereoscopic optical microscopy turns out to be indispensable for opthalmologic surgeries.

It is known for example from EP 0 697 611 A2 to combine an optical microscopy system with an OCT system. In this system, the light beam of the OCT system traverses the objective lens of the optical microscopy system. However, in this system it is difficult to arrange a reflector which deflects the OCT-measuring light beam of the OCT system in order to guide it to and traverse the objective lens of the optical microscopy system, thus to be incident on the object without impairing the performance of the optical microscopy system.

An object of the present invention is to provide a microscopy system that integrates an optical microscopy system and an OCT system that reduces the disadvantages of the prior art mentioned above.

It is a further object of the present invention to provide a microscopy system combining an optical microscopy system and an OCT system, wherein a capability and performance of the optical microscopy system is not impaired by the presence of the OCT system and vice versa.

It is a further object of the present invention to provide an optical system enabling microscopic examination, OCT and measurement of a wavefront of wavefront measuring light returned from an object.

An even further object of the present invention is to provide a surgical microscopy system particularly suitable for opthalmologic surgeries.

BRIEF SUMMARY OF THE INVENTION

The present invention has been accomplished taking the above problems into consideration.

According to an embodiment of the present invention, a surgical microscopy system having an optical coherence tomography (OCT) facility is provided, wherein the system comprises microscopy optics for generating an image of a first object region. The microscopy optics comprises an objective lens. The surgical microscopy system further includes an OCT system providing an OCT beam path and comprising a OCT-measuring light source, a reflector, imaging optics disposed between the light source and the reflector, and the imaging optics and a beam scanner disposed between the OCT-measuring light source and the imaging optics, wherein the reflector is configured and arranged to reflect a beam of OCT-measuring light, supplied from the imaging optics, such that it traverses the objective lens and is directed onto the first object region, and wherein the imaging optics is configured and arranged such that a second object region located near the beam scanner is optically imaged into an image region located near the reflector.

The first object region may be located in an object plane of the microscopy optics. The microscopy optics is arranged to receive light from the illuminated first object region for imaging the first object region. The microscopy optics may comprise plural refractive and/or diffractive optical elements. The microscopy optics may be adapted for stereoscopic optical imaging. The microscopy optics may further comprise a camera for acquiring an image of the first object region. The image acquired by the camera may be displayed on displays such as a monitor or a head-mounted display.

The OCT system may be a time domain OCT system (TD-OCT) or a frequency domain OCT system (FD-OCT). Both types have a time encoded and a spatially encoded subtype, wherein a depth scan is either performed sequentially over time or simultaneously by employing a spatially resolving detector. All these different variants can be used with embodiments of the present invention. Depending on the type and subtype of OCT system, a number and a configuration of components comprised in the OCT system may vary. In the case of a TD-OCT system, the measuring light source comprises a broad band OCT-light source adapted for generating OCT-measuring light having a coherence length of several micrometers depending on the application. A same or similar OCT-measuring light source may be employed in a sub-type of the FD-OCT system, that is Fourier domain OCT, wherein OCT-measuring light reflected at the object and superimposed with reference light is spectrally separated to obtain a spectrum of the superimposed light. Structural information in different depths within the object may be gained by calculating a Fourier transform of the thus obtained spectrum. In the case of another sub-type of FD-OCT, that is swept source OCT, the OCT-measuring light source comprises a wavelength tunable light source such as a tunable laser. Other components may be varied as well.

The beam scanner may comprise one or more deflecting elements that are rotatable about axes directed in different directions, preferably perpendicular to each other.

The reflector may be a mirror and/or a prism, in particular a prism having a form of a cross section of an isosceles triangle. The reflector functions to reflect the beam of OCT-measuring light of the OCT system such that it traverses the objective lens and is then incident onto the first object region being the region that is imaged by the microscopy optics.

The imaging optics is designed to guide light rays emanating from a second object region to the image region located near the reflector such that the position of these rays in the image region is substantially independent of an angle within a particular range at which the rays emanated from the second object region. In particular, a position of the beam of the OCT-measuring light deflected by the beam scanner incident on the reflector is substantially independent of a direction in which the beam of the OCT-measuring light is deflected by the beam scanner within a particular range of directions. Thereby, the size of the reflector can be decreased to diminish vignetting of microscopy light. Thus, a disturbance of the beam path of the microscopy optics and a beam path of the OCT system can be reduced.

According to an embodiment of the present invention the system further comprises collimating optics disposed in the beam path between the OCT-light source and the imaging optics. The collimating optics may comprise refractive elements, such as a lens, and/or diffractive elements, such as a grating.

Between the OCT-light source and the imaging optics both the collimating optics and a beam scanner are disposed. These components may be arranged in the order OCT-light source, collimating optics, beam scanner, and imaging optics. In other embodiments these components are arranged in the order OCT-light source, beam scanner, collimating optics and imaging optics. Thus, positions of the components beam scanner and collimating optics may be switched according to requirements of the application.

According to an embodiment of the present invention a center of the reflector is disposed at the image region and at least one deflecting surface of the beam scanner is disposed a distance $d_1$ away from the second object region optically corresponding to the image region, wherein the following relations hold:

$$d_1 = A/\beta^2 \text{ and}$$

$$0 \text{ mm} \leq A \leq 200 \text{ mm},$$

wherein $\beta$ is a magnification of the imaging optics.

Distances between optical elements, between regions, or between a region and an optical element are measured along an optical axis of the OCT-system, such as along the OCT beam path. Such optical axis may be defined as the center of the beam of OCT-measuring light traversing the OCT-system. Thus, whenever measuring distances are concerned, a position of an optical element is considered to be a point, where the center of the beam of measuring light is incident at the optical element.

Choosing the image region of the imaging optics at the center of the reflector defines the location of the second object region according to parameters of the imaging optics. Disposing at least one deflecting surface of the beam scanner at most in a distance $d_1$ away from the second object region as defined above ensures that the deflected beam of measuring light is imaged by the imaging optics to a location at most a distance A away from the reflecting portion of the reflector. The magnification $\beta$ is obtained from parameters of the imaging optics, such as focal length of lenses forming the imaging optics.

According to an embodiment of the present invention $A \leq 160$ mm, in particular $A \leq 120$ mm, further in particular $A \leq 100$ mm.

According to an embodiment of the present invention, a magnification $\beta$ of the imaging optics is changeable. Thus, when changing the optical parameters of the microscopy optics, such as by replacing a first microscopy optics by a second microscopy optics, is becomes possible by adjusting the magnification of the imaging optics to maintain a spot size of the OCT-measuring light beam at the first object region, such that a lateral resolution of the OCT-system is unchanged.

Alternatively, when the microscopy optics is unchanged, it is possible by adjusting the magnification of the imaging optics to change the spot size of the OCT-measuring light beam at the first object region, in order to change the lateral resolution of the OCT-system.

According to an embodiment of the present invention, the imaging optics comprises an afocal system. In general, an afocal system is a system that does not focus parallel light rays traversing the afocal system, but may alter a cross sectional size of a beam of parallel light rays travelling through it. The afocal system is in particular useful, when the beam of OCT-measuring light formed by the collimating optics is comprised of a bundle of parallel light rays. In this case, the beam of OCT-measuring light deflected by the beam scanner is incident on the imaging optics, i.e. the afocal system, as a bundle of parallel light rays.

According to an embodiment of the present invention, the imaging optics is a Kepler telescope. A Kepler telescope is made from two lenses or lens groups with positive refractive power, wherein a distance between both lenses substantially matches the sum of their focal lengths. A Kepler telescope may image an object disposed in the focal plane of the first lens to an image region in a focal plane of the second lens. However, it is not necessary that the object or image planes coincide with the focal planes of the lenses. As it is well-known from optical design textbooks, when the object plane is moved apart from the focal plane of the first lens by a first distance, also the image region moves apart from the focal plane of the second lens by a second distance that may be derived based on the first distance and a magnification of the Kepler telescope.

According to an embodiment of the present invention, the beam scanner comprises a deflecting surface which is in two different directions independently pivotable and wherein $A \leq 50$ mm. By this provision the beam scanner is configured as a so-called 3D scanner. It is advantageous to dispose this type of beam scanner more closely to the second object region, in order to reduce movement of an incident position of the beam of OCT-measuring light at the reflector during scanning the beam of OCT-measuring light.

According to an embodiment of the present invention, the beam scanner comprises a deflecting surface independently pivotable about two scanning axes parallel to the deflecting surface, wherein the two scanning axes are transverse, in particular orthogonal, relative to each other and wherein $A \leq 50$ mm. Thereby, a particular simple 3D scanner is provided.

According to an embodiment of the present invention, the beam scanner comprises two deflecting surfaces disposed apart from each other by a distance, wherein the deflecting surfaces are pivotable independently from each other, and wherein for both deflecting surfaces it holds:

$$d_1 \geq 4 \text{ mm}/\beta.$$

According to an embodiment of the present invention, the beam scanner comprises a first and a second deflecting surface, wherein the first deflecting surface is pivotable about a first scanning axis parallel to the first deflecting surface, and wherein the second deflecting surface is pivotable about a second scanning axis parallel to the second deflecting surface, wherein the first and the second scanning axes are transverse, in particular orthogonal, relative to each other and wherein for both deflecting surfaces it holds:

$$d_1 \geq 4 \text{ mm}/\beta.$$

According to an embodiment of the present invention, the microscopy optics comprises a zoom system for changing a magnification of the microscopy optics. The zoom system may be arranged downstream of the objective lens of the microscopy optics.

According to an embodiment of the present invention, the OCT-beam path of the OCT system is outside of the zoom system. In particular, the beam of OCT-measuring light of the OCT system may not traverse the zoom system. Thus, the performance and functionality of the OCT system is not influenced, and thus not impaired by changing the magnification of the zoom system comprised in the microscopy optics.

According to an embodiment of the present invention, the surgical microscopy system comprises an opthalmologic lens for examining a retina of an eye of a patient.

The effective diameter of the reflector may be computed from parameters of the collimating optics and the imaging optics, but may substantially not depend on a rotation angle of scanning mirrors comprised in the beam scanner. The effective diameter of an optical element may in general be defined by the diameter of a cross sectional region of the corresponding element that allows incident light to traverse the corresponding optical element perpendicular to a plane of the cross section.

According to an embodiment the surgical microscopy system further comprises a wavefront sensor having a wavefront measuring light entrance; and a wavefront sensor imaging lens, wherein a beam path of wavefront measuring light traverses the objective lens, the imaging optics and the wavefront sensor imaging lens such that the first object region is imaged to the wavefront measuring light entrance of the wavefront sensor.

A wavefront sensor is a device for characterizing a shape of a wavefront of wavefront measuring light entering the wavefront sensor at the wavefront measuring light entrance. An example of a wavefront sensor is the Hartmann-Shack-sensor. The Hartmann-Shack-sensor comprises a microlens array and a positionally resolving light detector arranged within a focal plane of the microlens array. The microlens array comprises plural microlenses arranged in a plane side by side. The plane of the microlens array corresponds to the wavefront measuring light entrance of the Hartmann-Shack-sensor. Each microlens of the microlens array has positive optical power and focuses a portion of the wavefront measuring light entering the wavefront sensor to a location at the positional resolving detector. The position of the location at the positional resolving detector depends on an inclination of the wavefront of the portion of the wavefront measuring light traversing this particular microlens. The other microlenses analogously focus other portions of the wavefront measuring light entering the wavefront sensor to other locations at the positionally resolving detector.

The positions of the locations may be determined by image processing known in the art. From the determined positions of the focused portions of the wavefront measuring light plural inclinations of the wavefront at the wavefront measuring light entrance of the wavefront sensor may be derived. From the derived plural inclinations a shape of the wavefront of the wavefront measuring light entering the wavefront sensor at the wavefront measuring light entrance can be determined.

Instead of using a Hartmann-Shack-sensor other types of wavefront sensors may be employed, such as a wavefront curvature sensor, a common path interferometer, a shearing interferometer, and the like.

By traversal of the wavefront measuring light through the objective lens, the imaging optics and the wavefront sensor imaging lens the first object region is imaged to the wavefront measuring light entrance of the wavefront sensor. Thus, a shape of a wavefront of wavefront measuring light at the first object region can be deduced from a shape of the wavefront of wavefront measuring light entering the wavefront sensor at the wavefront measuring light entrance. Thereby, the wavefront measuring light entrance of the wavefront sensor may be arranged within a focal plane of the wavefront sensor imaging lens.

According to an embodiment the surgical microscopy system further comprises an actuator to move the wavefront sensor and the wavefront sensor imaging lens relative to the imaging optics. When the shape of the wavefront of wavefront measuring light at the first object region is substantially spherical, moving the wavefront sensor together with the wavefront sensor imaging lens relative to the imaging optics may compensate for the spherical part of the shape of the wavefront of the wavefront measuring light. Thus, a distance between an assembly of the wavefront sensor and the wavefront sensor imaging lens and the imaging optics may be adjusted such that the shape of the wavefront measuring light incident at the wavefront sensor light entrance is approximately spherical having a large radius of curvature, such as 1 m, preferably 5 m, such that it is approximately a plane. The opportunity to move the wavefront sensor and the wavefront sensor imaging lens relative to the imaging optics may increase the dynamic range of the system for wavefront measuring.

According to an embodiment the surgical microscopy system further comprises a wavefront measuring light source for generating the wavefront measuring light; and a partially reflecting face arranged in the beam path of the wavefront measuring light between the wavefront measuring light source and the wavefront sensor light entrance. Further, the partially reflecting face may be arranged between the wavefront sensor imaging lens and the wavefront measuring light source. Further, the partially reflecting face may be arranged between the wavefront sensor imaging lens and the wavefront measuring light entrance of the wavefront sensor. Before entering the wavefront measuring light entrance the wavefront measuring light may be transmitted through or reflected at the partially reflecting face. Before traversing the wavefront sensor imaging lens the wavefront measuring light originating from the wavefront measuring light source may be transmitted through or reflected at the partially reflecting face.

According to an embodiment the wavefront measuring light has a wavelength in a first wavelength range and the OCT-measuring light has a wavelength in a second wavelength range. The first wavelength range may be different from the second wavelength range. The first and the second wavelength ranges may overlap. Preferably they do not overlap.

According to an embodiment one of the wavefront measuring light and the OCT measuring light has a wavelength in one of a range from 800 nm to 870 nm, in particular a range from 820 nm to 840 nm, and a range from 1280 nm to 1340 nm, in particular in a range from 1300 nm to 1320 nm. Further, the other one of the wavefront measuring light and the OCT measuring light has a wavelength in the other one of the range from 800 nm to 870 nm and the range from 1280 nm to 1340 nm.

According to an embodiment the surgical microscopy system further comprises a dichroitic beam splitter arranged in the beam path of the wavefront measuring light between the wavefront sensor imaging lens and the imaging optics. In particular, the dichroitic beam splitter may be configured to selectively transmit light in the wave length range from 800 nm to 870 nm and selectively reflect light in the wave length range from 1280 nm to 1340 nm or may be configured to selectively reflect light in the wave length range from 800 nm 870 nm and to selectively transmit light in the wave length range from 1280 nm to 1340 nm.

The surgical microscopy system may be provided with additional components designed for analyzing different parts of a patient's eye. These components may include an opthalmologic lens to be disposed close to the patient's eye, and a reduction lens to be arranged between the opthalmologic lens and the objective lens of the microscopy optics. With these additional components, it is possible to investigate a posterior portion of the patient's eye. With these components retracted from the beam path of the microscopy optics on the other hand an anterior portion of the patient's eye can be visualized and analyzed.

BRIEF DESCRIPTION OF THE DRAWINGS

The forgoing as well as other advantageous features of the invention will be more apparent from the following detailed description of exemplary embodiments of the invention with reference to the accompanying drawings. It is noted that not all possible embodiments of the present invention necessarily exhibit each and every, or any, of the advantages identified herein.

DETAILED DESCRIPTION OF THE INVENTION

Figure 1:
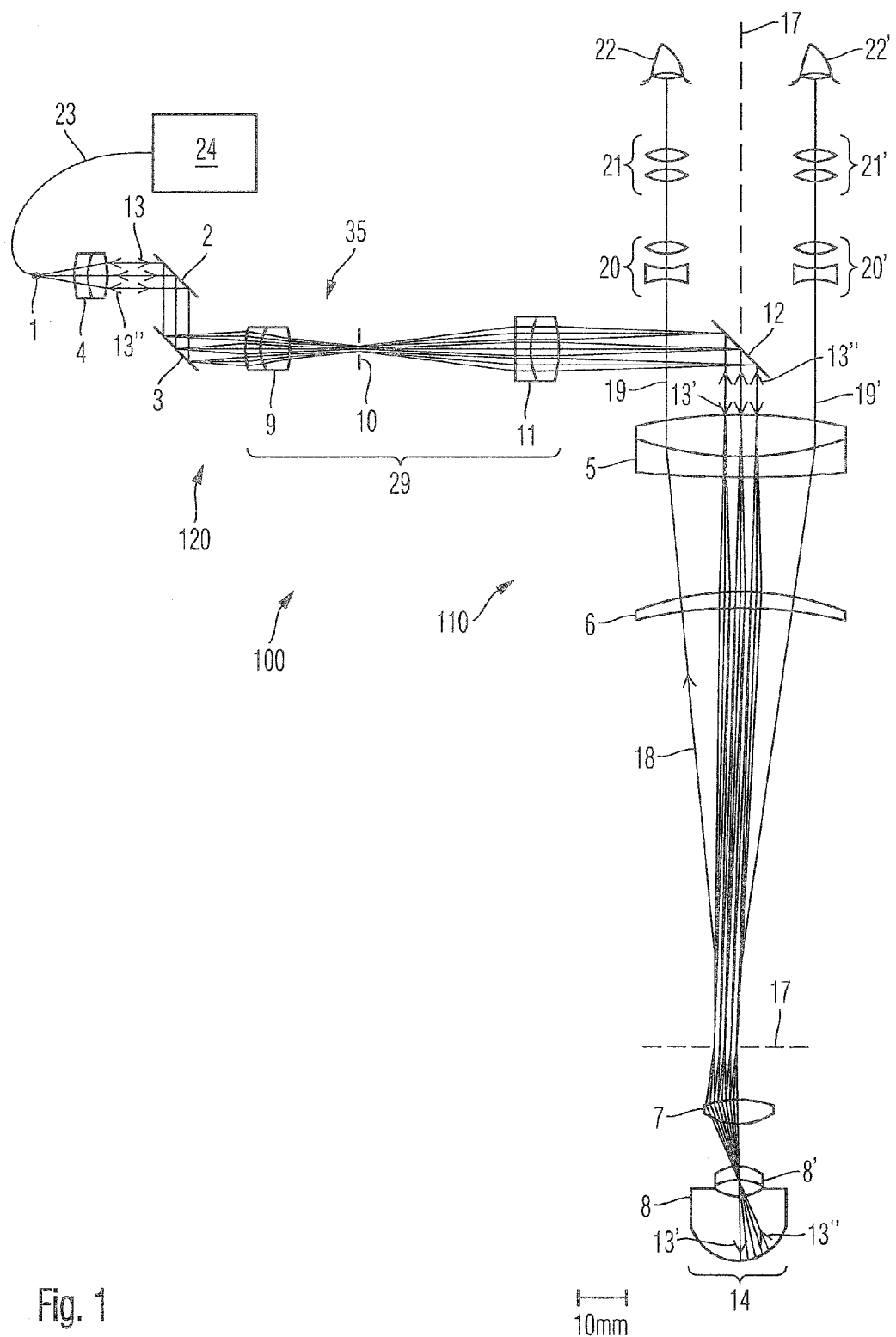
FIG. 1 schematically illustrates a surgical microscopy system according to an embodiment of the present invention.

In the exemplary embodiments described below, components that are alike in function and structure are designated as far as possible by alike reference numerals. Therefore, to understand the features of the individual components of a specific embodiment, the descriptions of other embodiments and of the summary of the invention should be referred to.

FIG. 1 schematically illustrates a surgical microscopy system 100 according to the present invention. The surgical microscopy system 100 is comprised of microscopy optics 110 and an OCT system 120.

The microscopy optics 110 images a first object region 14, in this case a retina of a patient's eye 8, to a retina of a left eye 22a and a retina of a right eye 22b of a user of the microscopy system. For this purpose, the patient's eye 8 is illuminated with illumination light generated by a not illustrated illumination light source. Depending on the application, the illumination light source may be a xenon light source or a halogen light source or the like. Light emanating from the first object region 14 traverses the patient's eye lens 8', traverses the ophthalmic lens 7 to form an intermediate image in the intermediate image plane 17. Light 18 emanating from the intermediate image in the intermediate image plane 17 traverses the reduction lens 6 and travels through the objective lens 5. Downstream of the objective lens 5 a parallel light beam 19 is formed which is separately guided into two tubes, a left tube and a right tube comprising a left zoom system 20 and a right zoom system 20', respectively, as well as a left ocular system 21 and a right ocular system 21', respectively. Thus, the left beam 19 is received by the user's left eye 22 and the right beam 19' is received by the user's right eye 22'. Reference numeral 17 indicates an optical axis of the microscopy optics 110.

The OCT system 120 comprises components for generating and guiding a beam of OCT-measuring light 13 as well as components for generating a reference beam, interferometrically superimposing the reference beam with a beam 13" reflected from the object 8 as well as components to detect the superimposed light beams.

A OCT-measuring light source generates OCT-measuring light in a broad spectral wavelength range having a peak wavelength of $\lambda=840$ nm. The OCT-measuring light is guided through a fiber 23 and is emitted by a fiber tip 1. The OCT-measuring light is formed by a Gaussian beam. The dispersion of the Gaussian beam behind the fiber tip is $\Theta=0.107$ rad. The OCT-measuring light emitted by the fiber tip 1 traverses collimating optics 4 to form a substantially parallel beam of OCT-measuring light 13. The beam of OCT-measuring light 13 is subsequently deflected by a first scanning mirror 2 to deflect the beam of OCT-measuring light 13 towards a second scanning mirror 3. The distance between the scanning mirrors is 8 mm in the illustrated embodiment. In other embodiments of the present invention the beam of OCT-measuring light first traverses the two scanning mirrors 2, 3 and then traverses the collimating optics 4.

Figure 3:
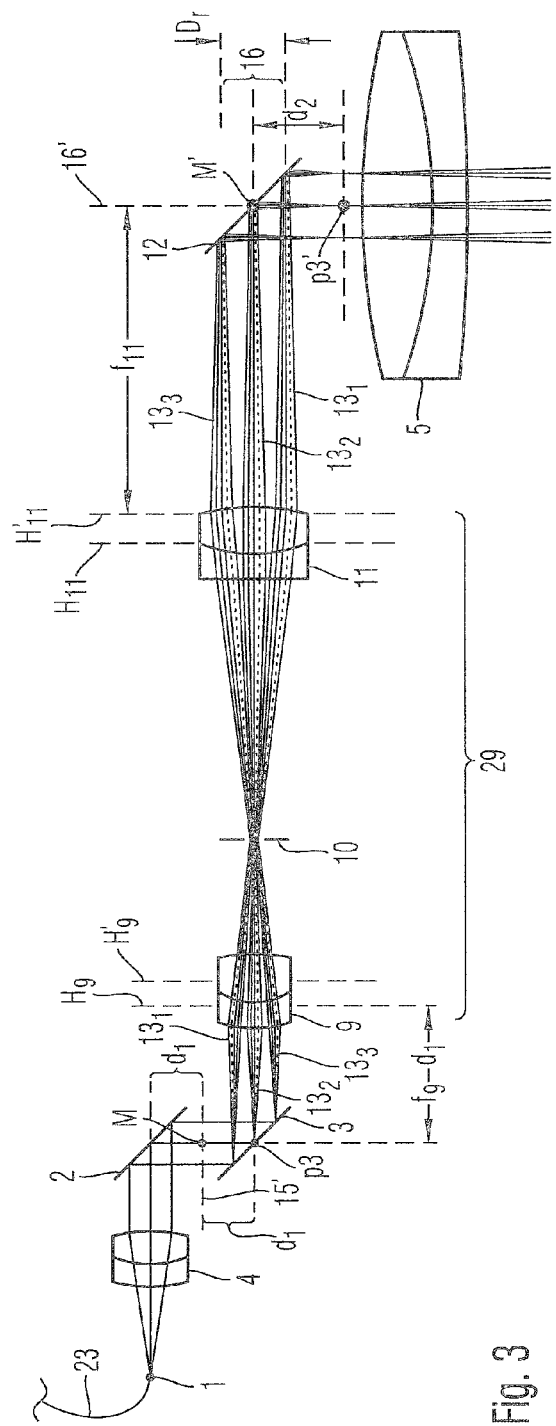
FIG. 3 schematically illustrates a portion of a surgical microscopy system illustrated in FIG. 1.

In order not to obscure the drawings, fiber tip 1, collimating optics 4 and scanning mirror 2 are not correctly depicted in FIGS. 1 and 3. Their proper orientation is obtained by rotating them for 90° out of the paper plane of FIGS. 1 and 3 about the connection line between both scanning mirrors 2 and 3. Scanning mirror 2 rotated for 90° out of the paper plane is rotatable about an axis in the paper plane that is horizontally oriented in FIG. 1. In contrast, scanning mirror 3 is rotatable about an axis perpendicular to the paper plane. Thus, the two rotation axes of scanning mirrors 2 and 3 are oriented perpendicular to each other.

The beam of OCT-measuring light 13 deflected by scanning mirrors 2 and 3 traverses the imaging optics 29. The imaging optics 29 is formed by a first lens group 9 and a second lens group 11 that are spaced apart by a distance of the sum of their focal lengths. Thus, the imaging optics 29 is designed as a Kepler telescope. Further, the beam of OCT-measuring light 13 is reflected at a reflector 12, traverses the objective lens 5, the reduction lens 6, the ophthalmic lens 7 of the microscopy optics 110 and the natural lens of the human eye 8 to be incident at the first object region 14 placed at an posterior portion of the eye 8.

In other embodiments the reduction lens 6 and the ophthalmic lens 7 of the microscopy optics 110 are withdrawn from the OCT-beam path and the beam path of the microscopy system. In this case the first object region 14 is placed at an anterior portion of the eye 8 such that for example the cornea or the anterior eye chamber can be investigated.

In embodiments of the present invention, where the beam of OCT-measuring light first traverses the two scanning mirrors 2, 3 and then traverses the collimating optics 4, the collimating optics can be considered to be part of the imaging optics 29, such that there is no separate collimating optics distinct from the imaging optics required.

The embodiment illustrated in FIG. 1 can be modified in a number of ways to provide a zoomable system: For example an afocal zoom system as is e.g. known from U.S. Pat. No. 5,991,090 or DE 198 37 135 A1 may be arranged between the collimating optics 4 and the beam scanner formed by scanning mirrors 2 and 3. A further modification can be achieved by replacing the Kepler telescope formed by lenses 9 and 11 by an afocal zoom system as is known from e.g. U.S. Pat. No. 5,991,090 or DE 198 37 135 A1. An even further modification comprises replacing the collimator 4 by a zoom system known from conventional photography.

By these measures, the spot size of the beam of OCT-measuring light can be adjusted appropriately.

OCT-measuring light reflected at the object at different depths of the object 8 traverses the ophthalmic lens 7, the reduction lens 6, the objective lens 5, is reflected by the reflector 12, traverses the imaging optics 29, is deflected by the scanning mirrors 2 and 3, traverses the collimating optics 4 and enters the fiber tip 1. Thus, the beam of OCT-measuring light returning from the probe arm 35 of the OCT-system 120 is guided by the fiber 23 to the Fourier-domain OCT illumination and analysis system 24. Within the analysis system 24 the beam of measuring light returned from the probe arm 35 is interferometrically superimposed with a reference beam. The superimposed light is dispersed into a frequency spectrum by a spectrometer. A distribution of reflectivities in different depths (axial direction) of the object 8 at a certain area in a lateral plane can be obtained by Fourier transformation of the spectrum.

In order to acquire structural information about the object across a region in the lateral plane the beam of measuring light 13 needs to be deflected to be directed to different areas within that region in the lateral plane. Therefore, the beam of measuring light 13 is scanned across the object 8 using the scan mirrors 2 and 3.

Details of the scanning system are illustrated with reference to FIG. 3. FIG. 3 schematically illustrates a part of the surgical microscopy system 100 illustrated in FIG. 1. In particular, a OCT beam path of the OCT system 120 leads from the fiber tip 1 emitting OCT-measuring light to the reflector 12 which reflects the beam of OCT-measuring light such that it traverses the objective lens 5 of the microscopy optics 110. The fiber tip 1, the collimating optics 4, the scanning mirror 2 and the scanning mirror 3, the lens group 9, the lens group 11 and the reflector 12 are configured such that a point M in the middle of the connecting line between the centers of the scanning mirrors 2 and 3 in a plane 15' is mapped to a point M' in the middle of the reflector 12 within a plane 16' comprising an image region 16.

In FIG. 3 $H_9$, $H_9'$ denote principal optical planes of the lens group 9 and $H_{11}$, $H_{11}'$ denote principal optical planes of the lens group 11. To more comprehensibly illustrate a OCT beam path of the OCT scanning system, bundles $13_1$, $13_2$ and $13_3$ (each formed by five rays corresponding to different rotational orientations of the scanning mirror 3) being incident on scanning mirrors 2 and 3 at three different positions are illustrated in FIG. 3. Each of these bundles $13_1$, $13_2$ and $13_3$ is deflected at the scanning mirror 3 and traverses the imaging optics (comprised of lens groups 9 and 11) resulting in bundles $13'_1$, $13'_2$ and $13'_3$. After being reflected at the beam reflector 12 bundles $13'_1$, $13'_2$ and $13'_3$ are imaged to an image region located in a plane displaced by a distance $d_2$ from the point M' in the middle of the reflector 12. In particular, a point p3 in the middle of the scanning mirror 3 is imaged to a point p3' located downstream the reflector 12. An analogous point in the middle of the scanning mirror 2 is imaged to a point upstream the reflector 12.

The imaging optics 29 comprised of lens groups 9 and 11 forms an afocal system in this embodiment. By arranging this afocal system 9, 11 in the OCT-beam path of the OCT system 120, the beam of measuring light 13' does not move on the reflector 12 by more than Δ=0.8 mm upon rotating one of the scanning mirrors 2 and 3. In the illustrated exemplary embodiment, the distance between the scanning mirrors 2 and 3 is $2*d_1=d_S=8$ mm. The f-number of the Kepler telescope 9, 11 is k=5.14. The magnification of the objective lens 5 and the combination of the ophthalmic lens 7 and the reduction lens 6 (fundus imaging system, FIS) is $\beta_{FIS}=0.119$. The focal length of the eye on retina's side is $f_{eye}=22.5$ mm. The refractive index of vitreous humour of the eye is $n_{vitreous}=1.3$. The waist radius of the beam of measuring light 13' at the patient's retina is $w_{retina}=8.66$ μm.

Figure 2:
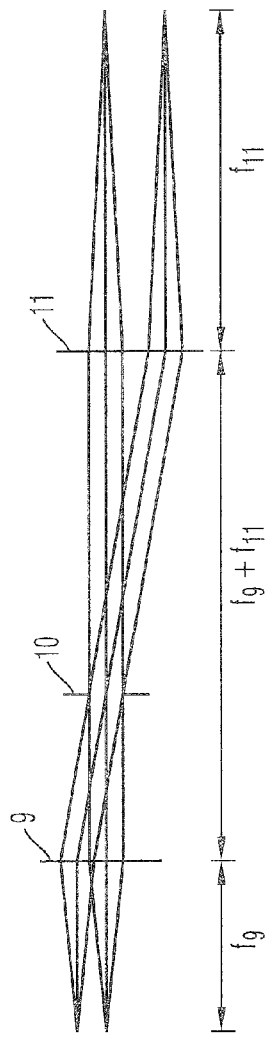
FIG. 2 schematically illustrates a beam path within the OCT facility of the surgical microscopy system according to an embodiment of the present invention.

In FIG. 2 the Kepler telescope comprised in the surgical microscopy system 100 illustrated in FIG. 1 is schematically illustrated. The Kepler telescope may in its simplest case be comprised of lenses 9 and 11 having positive refractive power. In FIG. 2 the focal length of lens 9 is indicated by $f_9$ and the focal length of lens 11 is indicated by $f_{11}$. The lenses 9 and 11 are disposed such that a distance between them is the sum of the focal lengths of both lenses, namely the distance is $f_9+f_{11}$. An object being disposed in a distance corresponding to the focal length of lens 9, i.e. $f_9$, upstream of lens 9 is imaged downstream the lens 11 at a distance apart from lens 11 corresponding to the focal length of lens 11, i.e. $f_{11}$. The object may also be disposed in distances from the lens 9 that are larger or smaller than the focal length $f_9$ of the lens 9. In this case the object will be imaged to a plane downstream of lens 11 that is disposed at a distance smaller or lager than $f_{11}$.

In the surgical microscopy system 100, the observations ray paths behind the objective lens 5 are parallel. The image plane for observation may coincide with the image plane for the OCT image. The OCT beam path downstream the objective lens may be nearly parallel.

The scanning mirrors 2, 3 should not be located in a convergent OCT beam path but preferably in a parallel OCT beam path. It may be disadvantageous to locate the scanning mirrors 2, 3 downstream and too close to the objective lens 5, because the OCT optical components may occupy a lot of space directly downstream the objective lens and could shadow light used for microscopic imaging. In order to minimize the space required for OCT components directly downstream the objective lens, an afocal system may be used which is located between the scanning mirrors 2, 3 and the objective lens 5. This afocal system may map a point M on an optical axis in the middle of both scanning mirrors 2, 3 to the center of the reflector 12. Thus, the space required for OCT components directly downstream the objective lens 5 may be minimized and the scanning mirrors may be located in a parallel OCT beam of OCT measuring light.

The afocal system may provide a real image of point M, because the center of the reflector may be positioned at this image. The most simple afocal system which fulfills this property may be a well-known Kepler telescope which is made from two lenses 9, 11 with positive refraction power where the distance between both lenses matches the sum of their focal lengths. FIG. 2 schematically shows a Kepler system which images the focal plane of the first lens 9 to the focal plane of the second lens 11. Of course, it is not necessary that the object or image planes coincide with the focal planes of the lenses. As it is well-known from optical design textbooks, when the object plane (left in FIG. 2) is moved for the distance $l_{object}$ to the right or left, also the image plane moves to the right or left for the distance $$l_{image} = \beta^2 \cdot l_{object} \quad (1)$$

with $$\beta = \frac{f_{11}}{f_9}$$

where $\beta$ is the lateral magnification of the Kepler telescope, $\beta^2$ is the corresponding longitudinal magnification and $f_9$ and $f_{11}$ are the focal lengths of the lens elements building up the Kepler telescope.

When the imaging optics in other embodiments of the present invention is not formed by a Kepler telescope, the magnification $\beta$ depends not only on optical parameters of the imaging optics, such as focal lengths, but also on the distance of the object and the image of the object from principal planes of the imaging optics. However, also in the general case the relationship $$l_{image} = \beta^2 \cdot l_{object} \text{ holds.}$$

Within the OCT system 120, a Gaussian beam emitted by the fiber tip 1 may be imaged onto the retina at 14, thereby the position of the waist may coincide with the position of the retina. A usual measure for the lateral resolution of the OCT system at the retina is the waist radius $w_{retina}$ from the OCT path at the retina. However, considerations concerning the paraxial optical layout may be simplified by replacing the Gaussian beam by a light bundle with an aperture matching the divergence of the beam at the retina. The numerical aperture NAO of this light bundle at the retina is given by $$NAO = \frac{\lambda}{w_{retina} \cdot \pi}$$

For the time being, we consider a ray bundle starting at the retina with numerical aperture NAO. Then, the radius of the parallel ray bundle in front of the eye is $$r_{eye} = NAO \cdot \frac{f_{eye}}{n_{vitreous}}$$

$$= \frac{\lambda}{w_{retina}} \cdot \frac{f_{eye}}{\pi \cdot n_{vitreous}}$$

where $f_{eye}$ is the focal length of the eye on retina's side and $n_{vitreous}$ is the refractive index of the vitreous humor of the eye.

The focal length of the objective lens 5 and the FIS consisting of a reduction lens 6 and an ophthalmic lens 7 are considered to be given from application specific constraints. These three components may also form an afocal system which converts a parallel ray bundle with radius $r_{eye}$ in front of patient's eye to a parallel ray bundle with radius $$r_{11} = \frac{r_{eye}}{\beta_{FIS}} \quad (2)$$

$$= \frac{\lambda}{w_{retina} \cdot \beta_{FIS}} \cdot \frac{f_{eye}}{\pi \cdot n_{vitreous}}$$

between the second lens group 11 of the Kepler telescope and the objective lens 5. Thus, a relation between the focal length $f_{11}$ and the f-number k of the Kepler telescope may be written as $$f_{11} = 2 \cdot k \cdot r_{11} \quad (3)$$

As a rule of thumb, optical aberrations of a Kepler telescope may be sufficiently controlled, when the f-number k exceeds a value of 4. Thus, equation 3 may be regarded as giving a lower limit of the focal length $f_{11}$. Since the overall length of the OCT optical components may decrease with decreasing focal lengths $f_9$ and $f_{11}$, it may be an advantage to choose $f_{11}$ according to equation 3 with f-number $k \approx 4$.

Next, a reasonable value for the focal length $f_9$ may be determined. According to equation 1 and a given value $f_{11}$, the focal length $f_9$ may determine the longitudinal magnification $\beta^2$. Since we may need two scanning mirrors with mutual distance $d_S$, it may be impossible to image both mirrors simultaneously onto the reflector 12 by the Kepler telescope. In order to keep the reflector 12 as small as possible, the image of the first scanning mirror 2 may be located in a distance d upstream of the reflector 12, whereas the second scanning mirror 3 may be located in a distance d downstream of the reflector 12. Using equation 1, one obtains $$d = \frac{1}{2} \cdot \beta^2 \cdot d_s$$
$$= \frac{1}{2} \cdot \left(\frac{f_{11}}{f_9}\right)^2 \cdot d_s$$

Since none of the mirrors may be imaged exactly at the reflector, the central OCT ray may move by a distance $\Delta$ on the reflector, when one of the scanning mirrors is swinging. The distance $\Delta$ should be as small as possible in order to keep the reflector 12 downstream of the objective lens 5 as small as possible. The distance $\Delta$ can be derived as follows. A proper OCT specification may also define an angle $\gamma_{eye}$ which is the maximum angle of OCT light to the optical axis of patient's eye. The angle $\gamma_{eye}$ in front of the eye may require an angle $\gamma_{scan} = \gamma_{eye} \cdot \beta_{FIS}$ between the OCT light and the optical axis of the objective lens 5. Using the above relationships one derives $$\Delta = d \cdot \gamma_{scan}$$
$$= \frac{\gamma_{eye} \cdot \beta_{FIS}}{2} \cdot \left(\frac{f_{11}}{f_9}\right)^2 \cdot d_s$$

which may yield an expression for the focal length $f_9$ according to $$f_9 = f_{11} \cdot \sqrt{\frac{\gamma_{eye} \cdot \beta_{FIS} \cdot d_s}{2 \cdot \Delta}} \quad (4)$$

Finally, the focal length $f_4$ of the collimating optics 4 may be calculated according to $$f_4 = \frac{r_9}{\theta} = \frac{r_{11}}{\theta \cdot \beta}$$

where $r_9$ is the radius of the parallel OCT light bundle 13 at the first lens 9 of the Kepler telescope and $\theta$ is the divergence of the Gaussian beam emitted from the fiber tip 1. Using equation 1, we may get $$f_4 = \frac{r_{11} \cdot f_9}{\theta \cdot f_{11}} \quad (5)$$

Using the equations 2 to 5 may allow to derive an exemplary paraxial layout of the system 100 as detailed in table 1.

The optical data for the surgical microscopy system illustrated in FIGS. 1 and 3 are given in the following Table 1. Thereby the following abbreviations are used: trans for transmissive, refl for reflective, c for circular, r for rectangular and e for elliptical.

TABLE 1

| Surface | Curvature (mm) | Type | Thickness (mm) | Glass (Schott) | Aperture (mm) | Waist radius @ surface (μm) | Comment |
|---|---|---|---|---|---|---|---|
| S0 | 0. | trans | 17.22 | | | 2.5 | fiber tip 1 |
| S1 | 30.505 | trans | 4. | NSF66 | 8. c | 1842. | |
| S2 | 11.301 | trans | .4 | NSK2 | 8. c | 1954. | collimating lens 4 |
| S3 | −12.775 | trans | 6. | | 8. c | 2214. | |
| S4 | 0. | refl | 8. | | 7.2 × 9.4 r | | first scan mirror 2 |
| S5 | 0. | refl | 17. | | 7.2 × 9.4 r | | second scan mirror 3 |
| S6 | 20.097 | trans | 4. | NSF66 | 9.6 c | 2214. | |
| S7 | 7.7179 | trans | 7.2 | NLASF45 | 9.6 c | 2006. | Kepler lens element 9 |
| S8 | −52.708 | trans | 18. | | 9.6 c | 17.23. | |
| S9 | 0. | trans | 39.177 | | 5. c | 3.5 | aperture stop 10 |
| S10 | 530.88 | trans | 4. | NSF66 | 16. c | 3755. | |
| S11 | 19.387 | trans | 6.8 | SLAH60 | 16. c | 3945. | Kepler lens element 11 |
| S12 | −33.738 | trans | 46.723 | | 16. c | 4336. | |
| S13 | 0. | refl | 17. | | 10. × 14. c | | fold mirror 12 |
| S14 | 120.57 | trans | 10.5 | NPK52A | 53. c | 4319. | |
| S15 | −79.433 | trans | 5.1 | NBAF4 | 53. c | 4193. | main lens 5 |
| S16 | −266.07 | trans | 30. | | 53. c | 4153 | |
| S17 | 71.4961 | trans | 3.25 | NSK5 | 52. c | 3500. | reduction lens 6 |
| S18 | 100. | trans | 125.743 | | 52. c | 3397. | |
| S19 | 23.858 | trans | 5.780 | FK3 | 16. c | 434. | ophthalmic lens 7 |
| S20 | −10.5919 | trans | 11. | | 16. c | 522. | |
| | | | | Patient's Eye 8 | | | |
| Retina | | | | | | 10. | |

The focal length of the collimating optics 4 and the lens elements of the Kepler telescope 9, 11 may be derived under the following assumptions:

OCT peak wavelength: λ=840 nm;
Dispersion of Gaussian beam behind fiber tip 1: θ=0.107 rad;
Waist radius at the retina: $w_{retina}$=8.66 μm;
Max. angle of OCT light in front of patient's eye: $\gamma_{eye}$=25°*π/180°=0.436 rad;
Max. acceptable moving of OCT rays on reflector 12: Δ=0.8 mm;
Magnification of objective lens 5 and FIS: $\beta_{FIS}$=0.119 (according to table 1);
Distance between scanning mirrors 2, 3: $d_S$=8 mm;
f-number of Kepler telescope: k=5.14;
Focal length of the eye on retina's side: $f_{eye}$=22.5 mm;
Refractive index of vitreous humor of the eye: $n_{vitreous}$=1.33.

With these specification data and equation 2, the ray bundle radius between the objective lens 5 and the second lens element 11 of the Kepler telescope may be $$r_{11} = \frac{0.84\ \mu m}{8.66\ \mu m \cdot 0.119} \cdot \frac{22.5\ mm}{\pi \cdot 1.33} = 4.39\ mm$$

From equation 3, the focal length of lens element 11 may be $$f_{11} = 2 \cdot 5.14 \cdot 4.39\ mm = 45.1\ mm$$

From equation 4, one may obtain for the focal length of lens element 9

$$f_9 = 45.1\ mm \cdot \sqrt{\frac{0.436 \cdot 0.119 \cdot 8\ mm}{2 \cdot 0.8\ mm}} = 23.0\ mm$$

Finally, the focal length of the collimating optics 4 may be calculated according to equation 5:

$$f_4 = \frac{4.39\ mm \cdot 23.0\ mm}{0.107 \cdot 45.1\ mm} = 20.9\ mm$$

With focal lengths calculated above, the optical layout may be optimized. Then, the focal length may slightly be adjusted in order to adjust the waist radii as required. FIGS. 1 and 3 and table 1 show an optical design of an embodiment according to the current invention. In this design, the following focal lengths are realized: $f_4$=20.7 mm, $f_9$=23.1 mm and $f_{11}$=45.1 mm which are very close to the paraxial values. Table 1 also shows the waist radii on each surface.

Due to longitudinal chromatic aberrations of the objective lens 5, the FIS 6,7 and patient's eye 8, it may be necessary to focus the OCT light on the retina. In this embodiment, the second lens group 11 of the Kepler telescope may be moved along the optical axis for a short distance. This may allow to optimize the OCT signal to obtain an optimal lateral resolution of the OCT image.

In the surgical microscopy system illustrated in FIG. 1, the ophthalmic lens 7 and the reduction lens 6 can optionally be inserted into beam path of the microscopy optics or retracted from the beam path of the microscopy optics 110. Thereby, it is possible to observe using the microscopy optics and the OCT system either an anterior portion of the patient's eye 8, when the reduction lens 6 and the ophthalmic lens 7 are retracted, or a posterior portion of the patient's eye 8, when the reduction lens 6 and the ophthalmic lens 7 are inserted into the beam path of the microscopy optics. In both cases, using the OCT system 120, it is possible to obtain structural volume data of the respective portion of the patient's eye 8. Thus, the observer is provided with an optical image and at the same time with a representation of cross sectional structural data of the respective portion of the patient's eye 8 irrespective which portion of the patient's eye is examined.

Figure 4A:
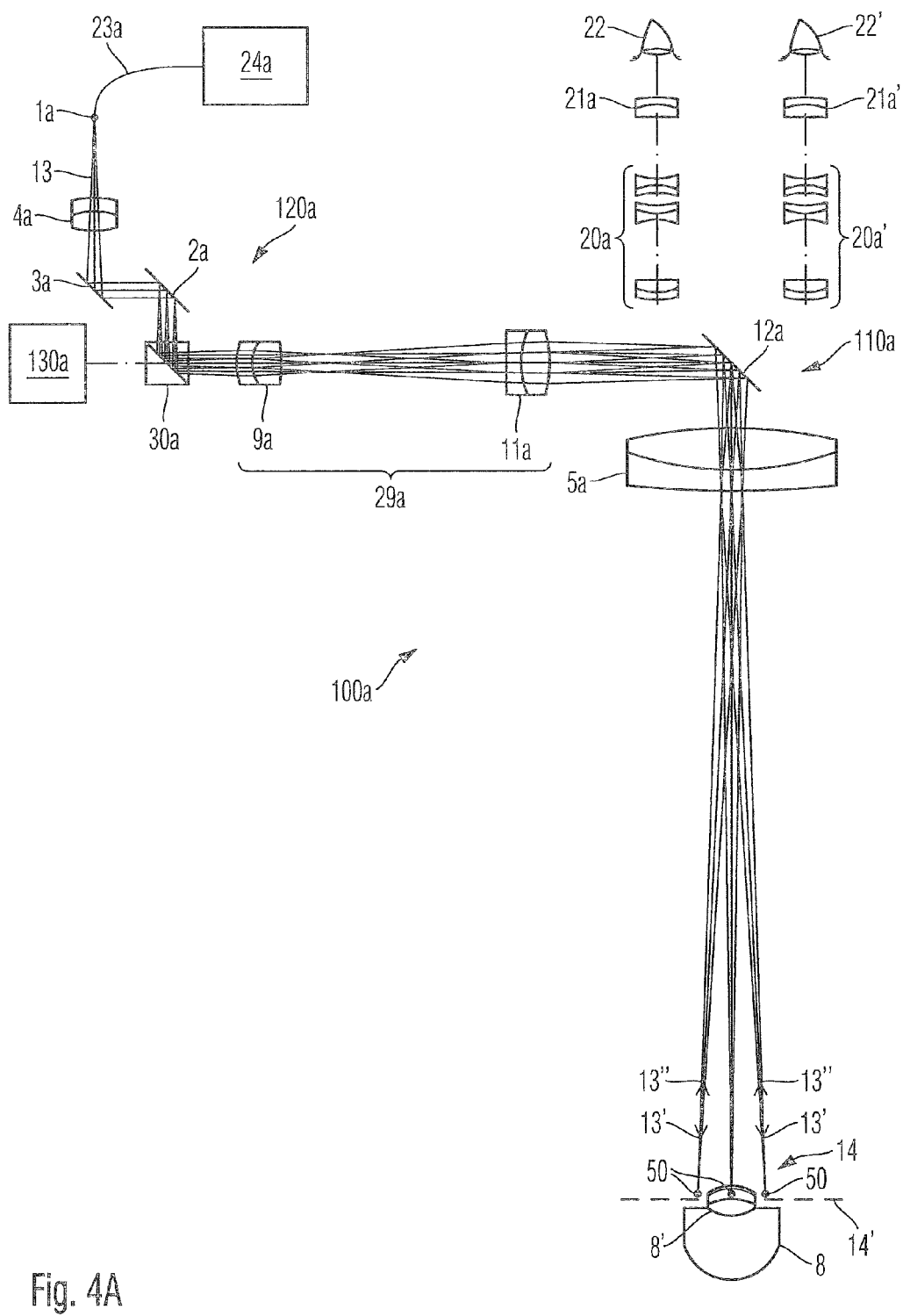
FIG. 4 schematically illustrates a further surgical microscopy system according to an embodiment of the present invention, in particular indicating the OCT beam path.
FIG. 4B illustrates the surgical microscopy system of FIG. 4A in particular indicating the beam path of the wavefront measuring light.
Figure 4B:
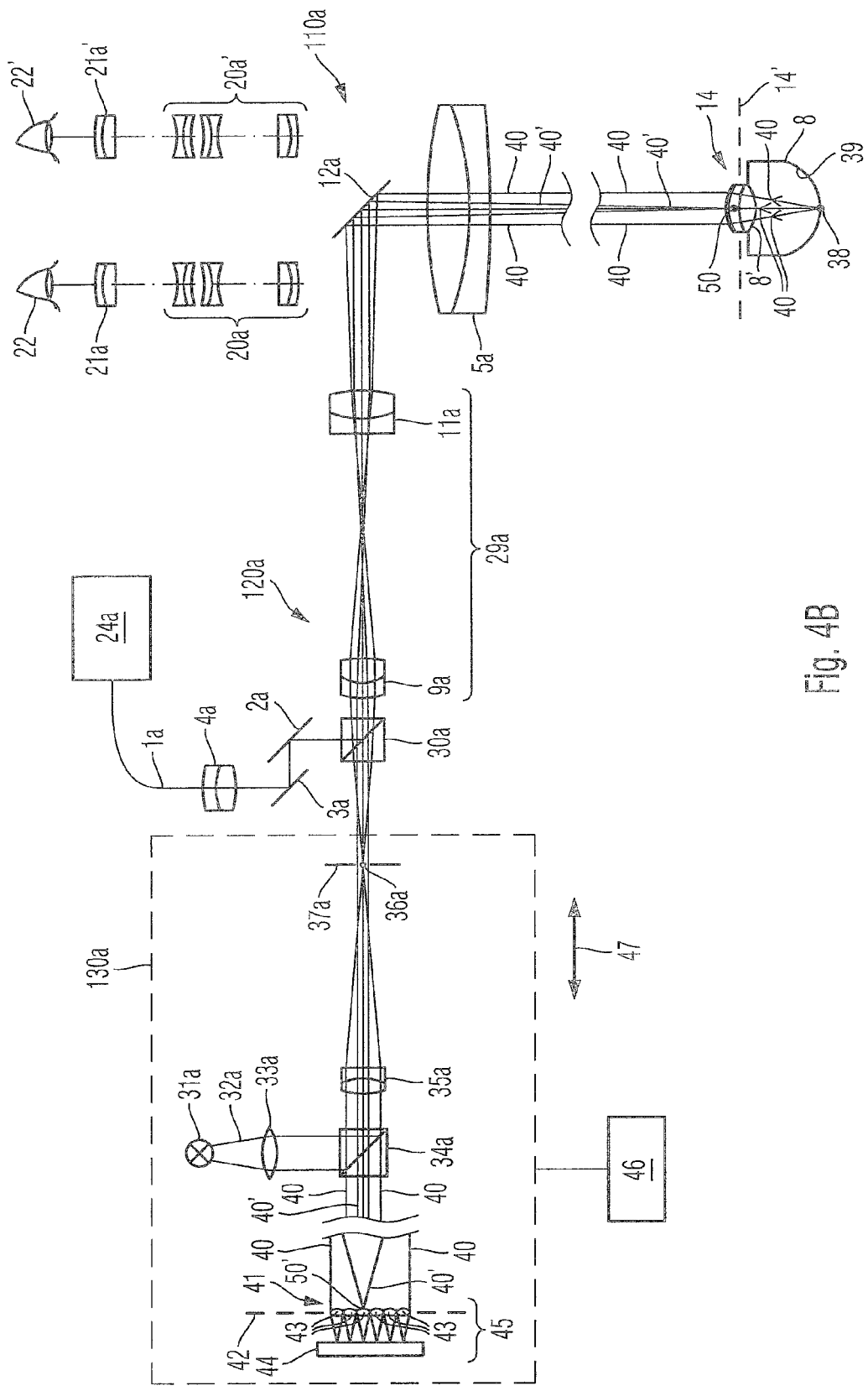

FIGS. 4A and 4B schematically illustrate a further surgical microscopy system 100a according to an embodiment of the present invention. Different from previously illustrated and described embodiments the surgical microscopy system 100a illustrated in FIGS. 4A and 4B additionally comprises a wavefront measuring system 130a.

Referring to FIG. 4A first the OCT system 120a is described in detail. The Fourier-domain OCT illumination and analysis system 24a comprises an OCT measuring light source which generates OCT measuring light 13. The OCT measuring light 13 is guided by optical fiber 23a to exit at fiber tip 1a. OCT measuring light 13 traverses collimating optics 4a which collimates the OCT measuring light 13 to substantially plane wavefronts. OCT measuring light 13 is then reflected at scan mirror 3a and scan mirror 2a which are pivotable about axes perpendicular to each other. In FIG. 4A beam paths of the OCT measuring light for three different pivoting positions of scan mirror 2a are illustrated. The OCT measuring light comprising wavelengths in a range from 1280 nm to 1340 nm, in particular from 1300 nm to 1320 nm, is reflected at the dichroitic beam splitter 30a which reflects this wavelength range with high efficiency. The OCT measuring light 13 then traverses the imaging optics 29a configured as an afocal system. The imaging optics 29a comprises the lens group 9a and the lens group 11a which are spaced apart by a distance corresponding to the sum of their focal lengths. Thus, the lens group 9a and the lens group 11a together form a Kepler system. In particular, the imaging optics 29a is configured and arranged such that a point between the two scan mirrors 3a and 2a is imaged to a center of the reflector 12a, as described in detail above in particular referring to FIG. 3.

The OCT measuring light 13' having traversed the imaging optics 29a is reflected at the reflector 12a such that it traverses the objective lens 5a and is incident onto the first object region 14 comprised in an object plane 14', where an anterior portion of an eye 8 is placed. For the three pivoting positions of scan mirror 2a the fiber tip 1a is imaged to three different positions 50 at the first object region 14.

OCT measuring light 13' is reflected at the anterior portion of the eye 8 as OCT measuring light 13". OCT measuring light 13" traverses the same optical elements as OCT measuring light 13 but in reversed order to reach optical fiber tip 1a from where it is guided via optical fiber 23a to the Fourier domain OCT illumination and analysis system 24a. Within system 24a the OCT measuring light 13" returned from the object 8 is superimposed with reference light, detected and processed to obtain structural information about the object 8.

Similar as the embodiment illustrated in FIG. 1 the surgical microscopy system 100a comprises microscopy optics 10a comprising lens systems 20a and 20a' and lens systems 21a and 21a' for stereoscopic microscopic imaging of the first object region 14. Lens systems 20a and 21a form a zoom system for the eye 22 and lens systems 20a' and 21a' form a zoom system for the eye 22'. In FIGS. 4A and 4B an ocular between each zoom system and the respective eye is not illustrated.

The microscopic image and the structure data obtained by the OCT system 120a may be displayed in a superimposed manner.

Referring now to FIG. 4B the wavefront measuring system 130a comprised in the surgical microscopy system 100a is described in detail. The wavefront measuring system 130a comprises a wavefront measuring light source 31a, a wavefront sensor 45, a beam splitter 34a, and wavefront sensor imaging lens 35a.

The wavefront measuring light source 31a generates wavefront measuring light 32a having wavelengths in a range from 800 nm to 870 nm, in particular from 820 nm to 840 nm. The wavefront measuring light 32a traverses collimating optics 33a which transforms the wavefront measuring light 32a in substantially plane wavefronts. The wavefront measuring light 32a is reflected at a beam splitter 34a and traverses the wavefront sensor imaging lens 35a which focuses the wavefront measuring light 32a at a point 36a in the center of an aperture 37a. The aperture 37a is arranged away from the wavefront sensor imaging lens 35a by a distance that corresponds to a focal length of the wavefront sensor imaging lens 35a.

The wavefront measuring light 32a subsequently traverses the dichroitic beam splitter 30a which transmits the wavefront measuring light having wave lengths in a range from 800 nm to 870 nm to a high degree. The wavefront measuring light 32a subsequently traverses the imaging optics 29a, is reflected at the reflector 12a, traverses the objective lens 5a such that the wavefront measuring light 32a is incident onto the first object region 14 arranged in the object plane 14' substantially as plane wavefronts. The plane wavefronts of the wavefront measuring light 32a traverse the anterior portion of the eye 8, in particular comprising the cornea and the natural lens 8', to be focused at a point 38 at the retina 39 of the eye 8.

In other applications of the microscopy system an eye without a natural lens may be investigated, i.e. an eye free of a natural lens. This condition is reached after the natural lens has been removed during a cataract surgery. In this condition the eye has a strong spherical ametropia, but the measured shape of the wavefront will be indicative of what kind of intraocular lens must be inserted to restore an emmetropic eye.

Alternatively, the eye may comprise an intraocular lens which has been inserted during a cataract surgery. Thereby, using the microscopy system, it may determined whether the intraocular lens has be positioned correctly, in particular concerning correction of astigmatism, and whether the surgery will be successful.

The wavefront measuring light 32a is sharply focused at the point 38 only if the eye is emmetropic, that means only if the length of the eye corresponds to a focal length of the refractive components of the eye, in particular the cornea and the natural lens, and if these refractive components do not show other non-spherical aberrations. In this case the illumination point 38 at the retina 39 diffusely reflects wavefront measuring light 40 as substantially spherical wavefronts. The wavefront measuring light 40 reflected at the point 38 traverses the natural lens and the cornea, traverses the objective lens 5a, is reflected at the reflector 12a, traverses the imaging optics 29a, transmits the dichroitic beam splitter 30a and is focused at the point 36a in the center of the aperture 37a.

Subsequently the wavefront measuring light 40 traverses the wavefront sensor imaging lens 35a which transforms the wavefront measuring light 40 into substantially plane wavefronts, when the eye 8 is an ideal emmetropic eye which optical components do not have optical aberrations. The wavefront measuring light 40 enters a wavefront measuring light entrance 41 of a wavefront sensor 45. In FIG. 4B the wavefront sensor 45 is enlarged compared to the beam splitter 34a. The wavefront measuring light entrance 41 is situated in a plane 42 where an array of microlenses 43 is arranged. In a focal plane of the microlenses downstream the array of microlenses a positionally resolving detector 44 is arranged to detect positions of focused portions of the wavefront measuring light. Deviations of the positions of focused portions of wavefront measuring light from ideal positions indicate a deviation of a shape of wavefront measuring light 40 from the shape of plane wavefronts.

The first object region 14 comprising the object 8 is imaged by the objective lens 5a, the imaging optics 29a and the wavefront sensor imaging lens 35a to the wavefront measuring light entrance 41. In particular the point 50 at the first object region is imaged to the point 50' at the wavefront measuring light entrance 41 of a wavefront sensor 45, as illustrated by beam path 40'. Thus, the shape of the wavefront at the first object region 14 can be determined using the wavefront measuring system 130a comprised in the surgical microscopy system 100a.

Not only emmetropic eyes but also ametropic eyes may be investigated using the wavefront measuring system 130a. For this purpose the surgical microscopy system further comprises an actuator 46 which is adapted to move the wavefront sensor 45, the wavefront sensor imaging lens 35a, and aperture 37a relative to the imaging optics 29a along directions indicated by the double arrow 47. Thus, spherical ametropia of an eye to be investigated can be compensated for in order to determine non-spherical aberrations of the eye.

The microscopy system can be configured to utilize the structural information about the investigated object obtained by the OCT-facility to improve the accuracy of the measurement of the shape of the wavefront of the measuring light. One way is to measure a distance between the object and a reference face, such as an optical face of the objective lens of the microscopy system closest to the object, by the OCT-facility. The measured distance may be supplemented to the wavefront measuring data to improve the accuracy of the wavefront measurement.

A problem often occurring during conventional wavefront measurements is that the optical axis of the eye does not align with the optical axis of the wavefront measuring system. In this condition the point where the wavefront measuring light is focused at the retina is not close to the fovea and the wavefront measurement of the eye is strongly impaired. Using the structural data obtained by the OCT-facility the exact orientation of the eye, in particular the anterior portion of the eye, may be determined. The patient can then be asked to move his or her eye in order to ensure that the orientation of the eye is optimal for the wavefront measurement.

In the following tables 2 and 3 optical data of the optical components of the embodiment illustrated in FIGS. 4A and 4B are given (trans indicates transmissive; refl indicates reflective).

TABLE 2

| radius (mm) | modus | thickness (mm) | glass (Schott) | diameter (mm) | component |
|---|---|---|---|---|---|
|  |  | 10.176 |  |  | fiber tip 1a |
| 135.444 | trans | 1.217 | SFL6 | 2.5 |  |
| 6.699 | trans | 2.13 | LAKN22 | 2.5 | collimator 4a |
| −6.699 | trans | 4.808 |  | 2.5 |  |

TABLE 2-continued

| radius (mm) | modus | thickness (mm) | glass (Schott) | diameter (mm) | component |
|---|---|---|---|---|---|
| plan | refl | 8. | | 5. | scan mirror 3a |
| plan | refl | 7.091 | | 5. | scan mirror 2a |
| plan | trans | 4.7 | NBK7 | | |
| plan | refl | 4.7 | NBK7 | | beam splitter 34a |
| plan | trans | 3. | | | |
| 19.684 | trans | 5. | NSF66 | 4.7 | |
| 7.269 | trans | 5. | NLAF2 | 4.7 | lens group 9a |
| −24.181 | trans | 64.073 | | 4.7 | |
| −2037.585 | trans | 5. | NSF66 | 8. | |
| 40.229 | trans | 5. | NBAF10 | 8. | lens group 11a |
| −27.412 | trans | 36. | | 8. | |
| plan | refl | 17. | | 7.1 | |
| 120.57 | trans | 10.5 | NPK52A | 26.5 | |
| −79.433 | trans | 5.1 | NBAF4 | 26.5 | objective lens 5a |
| −266.07 | | 193. | | 26.5 | |

TABLE 3

| radius (mm) | modus | thickness (mm) | glass (Schott) | diameter (mm) | component |
|---|---|---|---|---|---|
| | | 41.602 | | | |
| | trans | 4. | NBK7 | | |
| | trans | 4. | NBK7 | | beam splitter 34a |
| | trans | 5. | | | |
| 35.289 | trans | 3. | NLAF2 | 4. | |
| −20.128 | trans | 2. | NSF6 | 4. | wave front sensor imaging lens 35a |
| −426.963 | trans | 47.179 | | 4. | |
| | trans | 35.078 | | | aperture 37a |
| | trans | 4.7 | NBK7 | | |
| | trans | 4.7 | NBK7 | | dichroitic beam splitter 30a |
| | trans | 3. | | | |
| 19.684 | trans | 5. | NSF66 | 4.7 | |
| 7.269 | trans | 5. | NLAF2 | 4.7 | lens group 9a |
| −24.181 | trans | 64.073 | | 4.7 | |
| −2037.585 | trans | 5. | NSF66 | 8. | |
| 40-229 | trans | 5. | NBAF10 | 8. | lens group 11a |
| −27.412 | trans | 36. | | 8. | |
| | refl | 17. | | 7.1 | reflector 12a |
| 120.57 | trans | 10.5 | NPK52a | 26.5 | |
| −79.433 | trans | 5.1 | NBAF4 | 26.5 | objective lens 5a |
| −266.07 | | 193. | | 26.5 | |

Changing a magnification of the zoom system 20, 21 in the surgical microscopy system does not affect a measurement of an object using the OCT system 120, since the beam path of the OCT system lies outside the zoom system 20, that means a beam of OCT measuring light 13 of the OCT path does not traverse the zoom system 20. In particular, a waist radius of the beam of OCT measuring light of the OCT system at the object may not change upon changing the magnification of the zoom system 20. As a consequence a lateral resolution and a brightness of the OCT volume data may not change upon changing the magnification of the zoom system 20.

Another advantage of the surgical microscopy system illustrated in FIGS. 1, 3, 4A and 4B is that an extension of the reflector 12, sometimes also called "fold mirror" in systems of that kind, can be set minimal as required by the lateral resolution to be achieved and required by optical elements other than the scanning mirrors. The reason is that a position of the beam of OCT measuring light 13 incident on the reflector 12 varies only by a small amount upon changing rotational positions of the scanning mirrors 2 and 3 and ideally does not move at all, such as for a 3D-scanner. Thus, using a reflector 12 having a minimal extension (that means minimal effective diameter $D_r$) compared to the one in conventional systems enables the integration of the OCT system into the surgical microscopy system having the constraint that the beam of OCT measuring light of the OCT system has to traverse the objective lens of the microscopy optics.

The surgical microscopy system is designed such that a pupil of the beam of OCT measuring light of the OCT system may be located in the proximity of the objective lens 5 of the microscopy optics. Therefore, more space for other ray paths of the surgical microscopy system may be available.

Further, the scanning mirrors 2 and 3 may be located at positions, where the beam of OCT measuring light 13 of the OCT system is comprised of a bundle of parallel light rays. Thus, deterioration of the OCT image quality by unwanted Doppler effects may be reduced, when the axes of the scanning mirrors are not perfectly aligned.

Alternatively, the relation between scanning mirror rotation and scan position of spot on the object are same for each scanning mirror.

The present invention is not limited to the exemplary embodiment illustrated in FIGS. 1 and 3 with the optical data given in Table 1. Instead, the focal length of the objective lens 5 may be changed. Usually, the focal length of the objective lens 5 may be between f=150 mm and f=250 mm. Further, the focal lengths of reduction lens 6 and ophthalmic lens 7 may be changed. Decreasing the focal length, the observer sees an increasing opening of the retina with decreasing magnification. Further, a field lens may be disposed near the beam stop 10 of the imaging optics to control the distance between the second lens group 111 and the reflector 12. Further, the Kepler telescope comprised of lens groups 9 and 11 may be replaced by an afocal zoom system where a magnification β is tunable. Also, the collimating optics 4 may be replaced by a zoom system. Thereby it may be possible to adapt the OCT system between fiber tip 1 and objective lens 5 for different focal lengths of the objective lens 5, reduction lens 6 and the ophthalmic lens 7.

Other modifications of the inventive surgical microscopy system concern an adjustment of a probe arm 35 and a reference arm of the OCT system. In general, to obtain OCT data, an optical path length and dispersion of the probe arm 35 and the reference arm of the OCT system should match within the coherence length of the measuring light. This may be achieved by enlarging the air space between collimating optics 4 and the first scanning mirror 2. For this purpose, between these elements also a plane and parallel plate of optical glass may be introduced.

Further, the two scanning mirrors 2 and 3 may be replaced by a single 3D scanning mirror as described in the publication of Y. Xu et al., "MEMS based non-rotatory circumferential scanning optical probe for endoscopic optical coherence tomography", Pro. Of SPIE, Vol. 6627 (2007). Therein other optical components of the OCT system described above are to be configured such that the center of the 3D scanning mirror is mapped to a region near the center of the reflector 12. In this case, equation 4 given above may no longer be needed and the focal length $f_9$ can be chosen in order to shorten the overall length of the components of the OCT system 120.

The present surgical microscopy system is not restricted to Fourier domain OCT as illustrated in the exemplary embodiment 100 of FIG. 1. The OCT system according to the inventive surgical microscopy system may employ any frequency domain OCT system, wherein depths scanning of the object is obtained by either disposing a spectrometer in the beam path of the beam of measuring light of the OCT system, using a wavelength tunable light source of the OCT system or a combination thereof. Further, OCT-system may be a Time-domain OCT-system.

Summarized, in a surgical microscopy system according to embodiments of the present invention an optical coherence tomography facility is integrated into a microscopy system. A beam of measuring light formed by collimating optics of an OCT system is deflected by a beam scanner, traverses imaging optics, and is reflected by a reflector such that the beam of measuring light traverses an objective lens of microscopy optics and is directed to an object region of the microscopy optics. A position of the beam of measuring light being incident on the reflector is substantially independent on a direction into which the beam of measuring light is deflected by the beam scanner. When traveling through the beam scanner, the beam of measuring light may be a bundle of substantially parallel light rays.

While the invention has been described with respect to certain exemplary embodiments thereof, it is evident that many alternatives, modifications and variations will be apparent to those skilled in the art. Accordingly, the exemplary embodiments of the invention set forth herein are intended to be illustrative and not limiting in any way. Various changes may be made without departing from the spirit and scope of the present invention as defined in the following claims.

What is claimed is:

1. A surgical microscopy system having an optical coherence tomography (OCT) facility, the system comprising:
   microscopy optics providing a microscopy beam path and configured to image an object region onto an image plane disposed in the microscopy beam path, the microscopy optics comprising an objective lens; and
   an OCT system comprising:
      an OCT-measuring light source,
      a reflector,
      imaging optics, and
      a beam scanner having a first deflecting surface, wherein the OCT system provides an OCT beam path extending between the OCT-measuring light source and the object region;
   wherein the reflector is disposed in the OCT beam path between the imaging optics and the object region, and
   wherein the imaging optics are disposed in the OCT beam path between the beam scanner and the object region and configured to image a first plane disposed at a distance from the first deflecting surface of the beam scanner measured along the OCT beam path onto a second plane disposed at a center of the reflector,
   wherein the beam scanner is disposed in the OCT beam path and outside the microscopy beam path between the OCT-measuring light source and the object region,
   wherein the objective lens is disposed in the OCT beam path and the microscopy beam path between the reflector and the object region, and
   wherein the following relations hold:

$d_1 = A/\beta^2$ and $0 \text{ mm} \leq A \leq 200 \text{ mm}$, wherein $d_1$ is the distance between the first plane and the first deflecting surface of the beam scanner measured along the OCT beam path and $\beta$ is a magnification of the imaging optics.

2. The surgical microscopy system according to claim 1 further comprising collimating optics disposed in the OCT beam path between the OCT-measuring light source and the imaging optics.

3. The surgical microscopy system according to claim 1 wherein
   the image plane is outside the OCT beam path.

4. The surgical microscopy system according to claim 1 wherein at least one of the following relations holds:

$A \leq 160 \text{ mm}$, $A \leq 120 \text{ mm}$, or $A \leq 100 \text{ mm}$.

5. The surgical microscopy system according to claim 1 wherein the magnification $\beta$ of the imaging optics is changeable.

6. The surgical microscopy system according to claim 1 wherein the imaging optics comprises an afocal system.

7. The surgical microscopy system according to claim 1 wherein the imaging optics is a Kepler telescope.

8. The surgical microscopy system according to claim 1 wherein the first deflecting surface is independently pivotable in two different directions and wherein A is less than or equal to 50 mm.

9. The surgical microscopy system according to claim 1 wherein the beam scanner further comprises
   a second deflecting surface, wherein the first and the second deflecting surfaces are spaced apart from each other and wherein each of the distances of the first plane from each of the first and the second deflecting surface are greater than or equal to 4 mm divided by $\beta$.

10. The surgical microscopy system according to claim 1 wherein the microscopy optics comprises a zoom system for changing a magnification of the microscopy optics.

11. The surgical microscopy system according to claim 10 wherein the OCT beam path is outside of the zoom system.

12. The surgical microscopy system according to claim 1 further comprising an ophthalmic lens for examining a retina of an eye of a patient, wherein the ophthalmic lens is disposed between the objective lens and the object region.

13. The surgical microscopy system according to claim 1 further comprising
   a wavefront sensor having a wavefront measuring light entrance; and
   a wavefront sensor imaging lens,
   wherein a beam path of wavefront measuring light traverses the objective lens, the imaging optics and the wavefront sensor imaging lens such that the object region is imaged to the wavefront measuring light entrance of the wavefront sensor.

14. The surgical microscopy system according to claim 13 further comprising an actuator to move the wavefront sensor and the wavefront sensor imaging lens relative to the imaging optics.

15. The surgical microscopy system according to claim 13 further comprising:
   a wavefront measuring light source for generating the wavefront measuring light; and
   a partially reflecting face disposed in the beam path of the wavefront measuring light between the wavefront measuring light source and the wavefront sensor light entrance.

16. The surgical microscopy system according to claim 13 wherein the wavefront measuring light has a wavelength in a first wavelength range and OCT-measuring light generated from the OCT-measuring light source has a wavelength in a second wavelength range.

17. The surgical microscopy system according to claim 16 further comprising a dichroic beam splitter disposed in the beam path of the wavefront measuring light between the wavefront sensor imaging lens and the imaging optics.

* * * * *